US005977319A

United States Patent [19]
Pope et al.

[11] Patent Number: 5,977,319
[45] Date of Patent: Nov. 2, 1999

[54] SPECIFIC BINDING MEMBERS FOR ESTRADIOL; MATERIALS AND METHODS

[75] Inventors: Anthony Richard Pope, Cambrdgeshire; Kevin Pritchard, Whittlesford; Andrew James Williams, Forest Gate; Kevin Stuart Johnson, Caldecote Highfields, all of United Kingdom

[73] Assignee: Cambridge Antibody Technology Limited, Cambridgeshire, United Kingdom

[21] Appl. No.: 08/958,201

[22] Filed: Oct. 21, 1997

Related U.S. Application Data

[60] Provisional application No. 60/028,897, Oct. 21, 1996.
[51] Int. Cl.$^6$ .......................... C07K 16/00; A61K 39/395
[52] U.S. Cl. .................................. 530/388.24; 424/145.1
[58] Field of Search .............................. 424/130.1, 138.1, 424/139.1, 141.1, 142.1, 178.1; 435/4, 7.1, 325, 326; 436/512, 547, 548; 530/387.1, 387.7, 358.24, 389.1, 389.2, 391.1

[56] References Cited

U.S. PATENT DOCUMENTS

| 4,200,436 | 4/1980 | Mochida et al. ...................... 23/230 B |
| 5,342,760 | 8/1994 | Baler et al. .............................. 435/7.92 |
| 5,663,054 | 9/1997 | Williams et al. ....................... 435/7.93 |

FOREIGN PATENT DOCUMENTS

| 0 120 694 A2 | 10/1984 | European Pat. Off. . |
| 0 125 023 A1 | 11/1984 | European Pat. Off. . |
| 0 184 187 A2 | 6/1986 | European Pat. Off. . |
| 0 239 400 A2 | 9/1987 | European Pat. Off. . |
| 0 239 400 B1 | 9/1987 | European Pat. Off. . |
| 2 188 638 | 10/1987 | United Kingdom . |
| WO 92/09965 A1 | 6/1992 | WIPO . |
| WO 94/13804 A1 | 6/1994 | WIPO . |

OTHER PUBLICATIONS

Aravelo, J.H. et al., "Three dimensional Structure of an Anti–steroid Fab' and Progesterone–Fab' Complex," *J. Molecular Biology*, 231:103–118 (1993).

Bird, R.E. et al., "Single–Chain Antigen–Binding Proteins," *Science*, 242:423–426 (Oct., 1988).

Clackson, T. et al., "Making antibody fragments using phage display libraries," *Nature*, 352:624–628 (Aug. 15, 1991).

Cook, B. et al., "Measurement of steroid hormone concentrations in blood, urine and tissues," In: *Steroid Hormones: a practical approach,* Practical Approach series, Chapter 1, Rickwood et al., (eds.), Oxford University Press, Oxford, pp. 1–65 (1989).

Gram, H. et al., "In vitro selection and affinity maturation of antibodies from a naive combinatorial immunoglobulin library," *Proc. Natl. Acad. Sci., USA,* 89:3576–3580 (Apr., 1992).

Holliger, P. et al., "Engineering bispecific antibodies," *Current Opinion in Biotechnology,* 4:446–449 (1993).

Holliger, P. et al., "Diabodies: Small bivalent and bispecific antibody fragments," *Proc. Natl. Acad. Sci., USA,* 90:6444–6448 (Jul., 1993).

Huston, J.S. et al., "Protein engineering of antibody binding sites: Recovery of specific activity in an anti–digoxin single–chain Fv analogue produced in *Escherichia coli,*" *Proc. Natl. Acad. Sci., USA,* 85:5879–5883 (Aug., 1988).

Marks, J.D. et al., "By-passing Immunization Human Antibodies from V–gene Libraries Displayed on Phage," *J. Molecular Biology,* 222:581–597 (1991).

Munro, S. et al., "An Hsp70–like Protein in the ER: Identity with the 78 kd Glucose–Regulated Protein and Immunoglobulin Heavy Chain Binding Protein," *Cell,* 46:291–300 (Jul., 1986).

Plückthun, A., "Antibody Engineering: Advances from the Use of *Escherichia coli* Expression Systems," *Bio/Technology,* 9:545–551 (Jun., 1991).

Pope, A. et al., "In vitro selection of a high affinity antibody to oestradiol using a phage display human antibody library," *Immunotechnology,* 2:209–217 (1996).

Reff, M.E., "High–level production of recombinant immunoglobulins in mammalian cells," *Current Opinion in Biotechnology,* 4:573–576 (1993).

Tomlinson, I.M. et al., "The Repertoire of Human Germline $V_H$ Sequences Reveals about Fifty Groups of $V_H$ Segments with Different Hypervariable Loops," *J. Molecular Biology,* 227:776–798 (1992).

Traunecker, A. et al., "Bispecific single chain molecules (Janusins) target cytotoxic lymphocytes on HIV infected cells," *EMBO J.,* 10(12):3655–3659 (1991).

Trill, J.J. et al., "Production of monoclonal antibodies in COS and CHO cells," *Current Opinion in Biotechnology,* 6:553–560 (1995).

Ward, E.S. et al., "Binding activities of a repertoire of single immunoglobulin variable domains secreted from *Escherichia coli,*" *Nature,* 341:544–546 (Oct. 12, 1989).

Winter, G. et al., "Man–made antibodies," *Nature,* 349:293–299 (Jan. 24, 1991).

Gibson, Toby James, Studies in the Epstein–Barr virus genome University of Cambridge: Ph.D. Dissertation, Date approved: Dec. 7, 1984, BLDSC No. D58257/85, University of Cambridge, MRC Laboratory of Molecular Biology.

Vaughn, T.J. et al., "Human Antibodies with Sub–nanomolar Affinities Isolated from a Large Non–immunozed Phage Display Library," *Nature Biotechnology,* 14(3):309–314 (Mar. 1996).

Carter, P., "Binders from the deepest vaults," *Nature Biotechnology,* 14(3):267 (Mar. 1996).

*Primary Examiner*—Paula K. Hutzell
*Assistant Examiner*—Timothy A. Worrall
*Attorney, Agent, or Firm*—Marshall, O'Toole, Gerstein, Murray & Borun

[57] ABSTRACT

The invention relates to specific binding members for estradiol and materials and methods relating thereto, in particular antibodies or binding domains thereof which have high affinities (low dissociation constants) for estradiol and low cross-reactivity for other steroids. The invention further provides means to make such binding members, assay methods for the detection and/or quantitation of estradiol, and nucleic acid encoding said binding members, which nucleic acid may be used for their production. Preferred binding members include those with CDR regions of the D12 antibody heavy and light chain domains (SEQ ID NO:2 and SEQ ID NO:12 respectively).

22 Claims, 7 Drawing Sheets

FIG. 1a VH DOMAINS

|  | | CDR1 | | CDR2 | | CDR3 | |
|---|---|---|---|---|---|---|---|
| D12 | EVQLVESGGGLVQPGGSLRLSCAASGVTFS | SHAMT | WVRQAPGKGLEWV | SGISGSGGDTYHADSVKG | RFTISRDNSKNTVYLQMNSLRAEDTAIYYCAIL | GVLNGFDI | WGQGTMVTVSS |
| 1C | EVQLVESGGGLVQPGGSLRLSCAASGVTFS | SHAMT | WVRQAPGKGLEWV | SGISGSGGDTYHADSVKG | RFTISRDNSKNTVYLQMNSLRAEDTAIYYCAIL | GVLNGFDI | WGQGTMVTVSS |
| 2G | EVNLRESGGGLVKPGGSLRLSCAASGFTFS | DYYMS | WIRQAPGKGLEWV | SAISGSGGNTYADSVKG | RFTISRDNSKNTLSLQMNSLRTEDTALYYCVK | GARAARAGGYFD | LWGRGTLVTVSS |
| 2Da | RVQLVESGGGLVQPGRSLRLSCAASGFTFD | DYAMH | WVRQAPGKGLEWV | SGISWNSGSIGYADSVKG | RFTISRDNAKNSLYLQMNSLRAEDTAVYYCAR | PLYPKGTQYDF | WGQGTLVTVSS |
| 2Db | EVQLVESGGGLVQPGRSLRLSCAASGFTFD | DYAMH | WVRQAPGKGLEWV | SGISWNSGSIGYADSVKG | RFTISRDNAKNSLYLQMNSLRAEDTAVYYCAR | PLYPKGTQYDF | WGQGTLVTVSS |

FIG. 1b V_L DOMAINS

```
           CDR1
D12   QSALTQPASVSGSPGQSITISC  TGTSSDVGGYKYVS  WYQQHPGKAPKLMIF
1C/2D QSALTQPASVSGSPGQSITISC  TGTSSDVGGYKYVS  WYQQHPGKAPKLMIF
2G    DIVMTQSPSSVSAAIGDTITITC RASHNFRSWLA     WYQVKPGEAPKPLIY
```

```
 CDR2                                                 CDR3
EVSNRPS  GVPNRFSGSKSGNTASLTISGLQVEDEADYYC  SSLTRRVTVI  FGGGTKLTVLG
EVSNRPS  GVPNRFSGSKSGNTASLTISGLQAEDEADYYC  SSLTRRVTVI  FGGGTKLTVLG
GAFTFQN  GVPSRFSGSGSGTEFSLTINSLQLDDFATYFC  QQAHSFPPT   FGGGTKLEIKR
```

FIG. 2
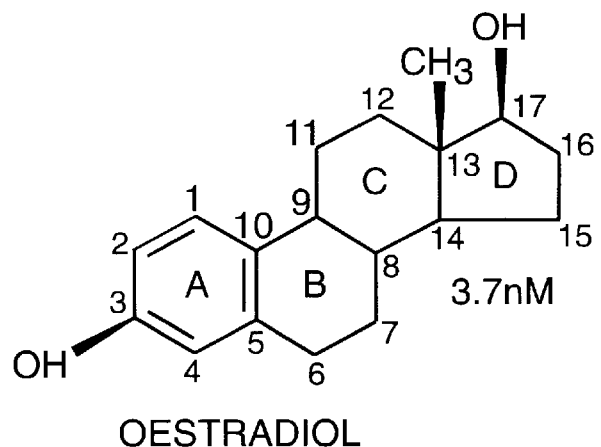
OESTRADIOL
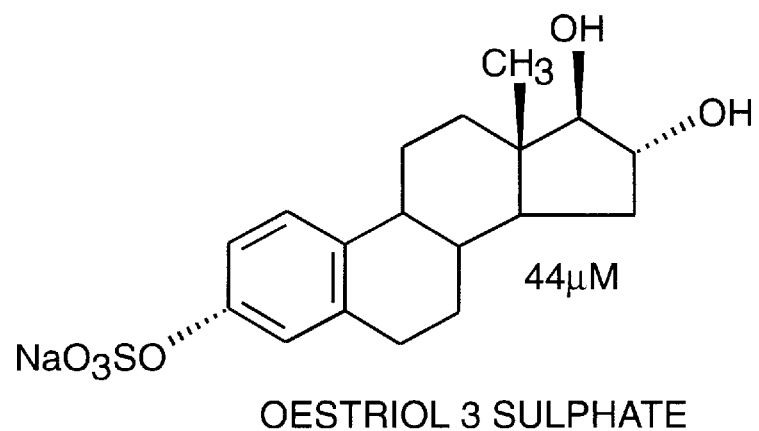
OESTRIOL 3 SULPHATE
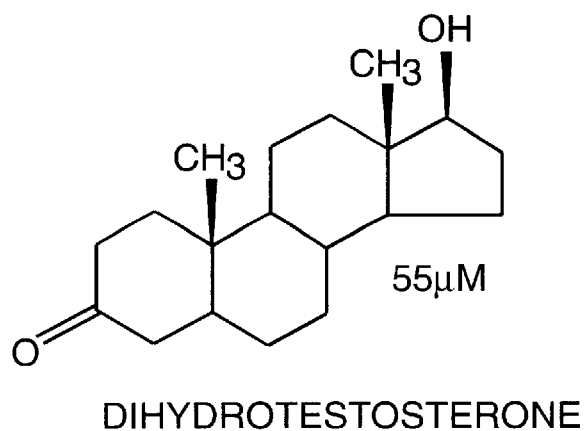
DIHYDROTESTOSTERONE

FIG. 2(contd)
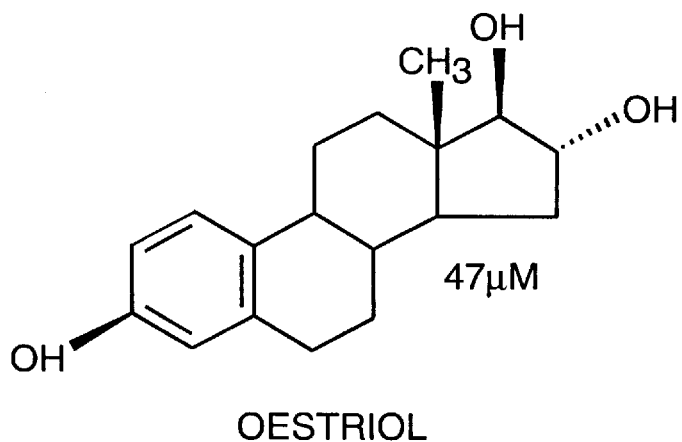
OESTRIOL
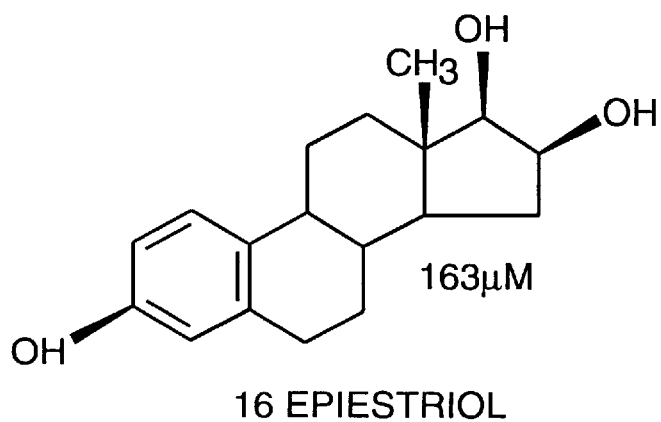
16 EPIESTRIOL
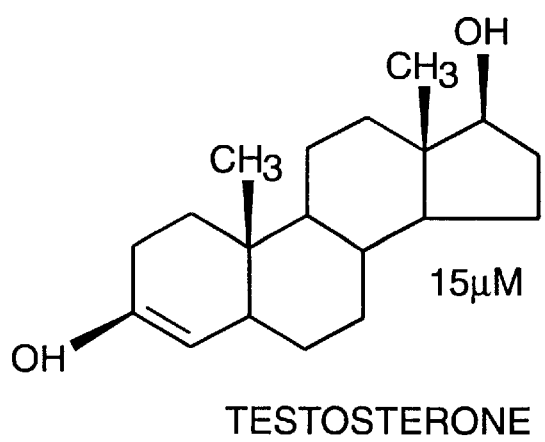
TESTOSTERONE

FIG. 4 pUC119Sfi POLYLINKER REGION

```
HindIII
AAGCTT TGGAGCCTT TTTTGGAGA TTTTCAAC GTG AAA AAA TTA TTA TTC GCA
                                     V   K   K   L   L   F   A
                     Signal sequence
                                                 SfiI
ATT CCT TTA GTT GTT CCT TTC TAT GCG GCC CAG CCG GCC ATG GCC CAG
 I   P   L   V   V   P   F   Y   A   A   Q   P   A   M   A   Q
                                                      NotI
GTC CAA CTG CAG GTC GAC CTC GAG ATC AAA CGG GCG GCC GCA GAA CAA
 V   Q   L   Q   V   D   L   E   I   K   R   A   A   A   E   Q
                              Myc tag
AAA CTC ATC TCA GAA GAG GAT CTG AAT GGG GCC GCA CAT CAC CAT CAT
 K   L   I   S   E   E   D   L   N   G   A   A   H   H   H   H
                                                         His tag
                  EcoR1
CAC CAT TAA TAA GGA TCC
 H   H   *   *
```

SPECIFIC BINDING MEMBERS FOR ESTRADIOL; MATERIALS AND METHODS

This application is based on provisional application Ser. No. 60/028,897, filed Oct. 21, 1996, from which priority is claimed and the contents of which are incorporated herein by reference.

FIELD OF THE INVENTION

This invention relates to specific binding members for estradiol and materials and methods relating thereto.

BACKGROUND OF THE INVENTION

Estradiol is one of a number of physiologically important steroid hormones among which minor differences in structure result in profoundly different biological activities [Cook, B. & Beastall, G. (1989). In "Steroid Hormones: a practical approach." Practical Approach Series (Rickwood, D. & Hames, B. D., eds.), Oxford University Press, Oxford. pp. 1–65.]. Measurement of estradiol levels in body fluids is important in clinical practice, for example to follow the menstrual cycle in women, and to monitor compliance and optimal dosing of estradiol administered as part of hormone replacement therapy in women at menopause. High levels of estradiol in men can be diagnostic of estrogen-secreting tumours such as Leydigs cell tumours, liver disease and hyperthyroidism.

Physiological concentrations of estradiol at particular stages in the menstrual cycle vary between individuals, but typically rise from around 0.18 nM at the lowest point to a peak of 1.5 nM prior to ovulation. These low levels of hormone make quantitative determination of estradiol difficult, placing a premium on the sensitivity and selectivity of assays. Antibody based detection methods are commonly used in diagnostic assays, but in the case of estradiol the antibody itself has proved to be the limiting factor.

Since steroids are not themselves immunogenic, they have to be coupled to a larger molecule in order to elicit an immune response in animals. However, it has been found that the antibodies raised in this way are often unable to recognise important structural differences in that part of the steroid attached to the carrier. The importance of specificity is not only in ensuring that the right hormone is measured, but also in discriminating between the biologically active form and metabolites inactivated by the liver [Cook, B. & Beastall, G. (1989)]. The inability to discriminate between closely related structures is manifested by the antibody having similar affinity for different steroids substituted at particular positions, and is often referred to as a 'blind-spot' [Aravelo, J. H., Stura, E. A., Taussig, M. J. & Wilson, I. A. (1993). J. Mol. Biol. 231, 103–118].

Useful polyclonal antisera have nevertheless been obtained [Cook, B. & Beastall, G. (1989)], though affinity and cross-reactivity of sera is highly variable between animals, creating problems in standardizing assays, and many animals need be immunised before an antiserum with the required properties is obtained, limiting the supply of serum. All currently available diagnostic kits use polyclonal, antisera (e.g. Abbott, Amersham etc.) Consequently, many attempts have been made to generate monoclonal antibodies. Although some have had high affinities (typically 50 nM or better), none has had the requisite specificity. The well-characterised mouse monoclonal antibody DB3 [Aravelo, J. H. et al.] binds to progesterone with a dissociation constant of approximately 1 nM. This antibody provides an excellent example of the properties of an antibody raised against a steroid coupled to a protein; although DB3 is specific to the portion of the steroid furthest from the carrier, it shows very little specificity at the end of the steroid that was conjugated to the protein and will bind equally well when even large substituents are present at this site.

Phage display has previously been used to isolate a progesterone-binding antibody from a non immunised murine repertoire [Gram, H., Marconi, L., Barbas, C. F., Collet, T. A., Lerner, R. A. & Kang, A. S. (1992). Proc. Natl. Acad. Sci. (USA) 89, 3576–3580.]. The dissociation constant of the resulting antibody was only micromolar, and cross-reactivity to other steroids was not explored.

SUMMARY OF THE INVENTION

Herein it is shown that large phage display libraries may be used as a source of antibodies specific for estradiol. Display on the surface of bacteriophage enables antibodies with desirable antigen binding characteristics to be selected from a mixed population of antibodies, together with the genes encoding them. Since the process is entirely in vitro, there is no requirement for immunisation.

In the work described herein, antibodies have been made and tested, showing high affinities (low dissociation constants) for estradiol and low cross-reactivity for other steroids. For the first time it has been shown to be possible to obtain antibodies which have high affinity for estradiol and discriminate between estradiol and other related steroids.

BRIEF DESCRIPTION OF THE DRAWINGS

FIG. 1 shows an alignment of the amino acid sequences of the antibody heavy chain variable domains (part (a)) and light chain variable domains (part (b)) of estradiol binding single-chain Fv molecules. The locations of the three CDR regions of each chain are indicated.

FIG. 2 shows structures and affinities of steroids recognised by antibody D12. Dissociation constants were measured by equilibrium dialysis using conditions described for testosterone and estriol (FIG. 3 and the description of FIG. 3 given below). All steroids were tested at concentrations ranging from 10 nM to their solubility limits in PBS. The dissociation constants of antibody D12 for these compounds were calculated assuming that they were competitive inhibitors of estradiol binding.

FIG. 4 shows the polylinker region (SEQ ID NO:17) and cloning sites of the phagemid vector pUC119Sfi. This vector is based on the vector pUC119 but with the original polylinker replaced by the one shown, using the Hind III and Eco RI sites.

DETAILED DESCRIPTION AND PREFERRED EMBODIMENTS

TERMINOLOGY

Specific binding member

Figure 3A:
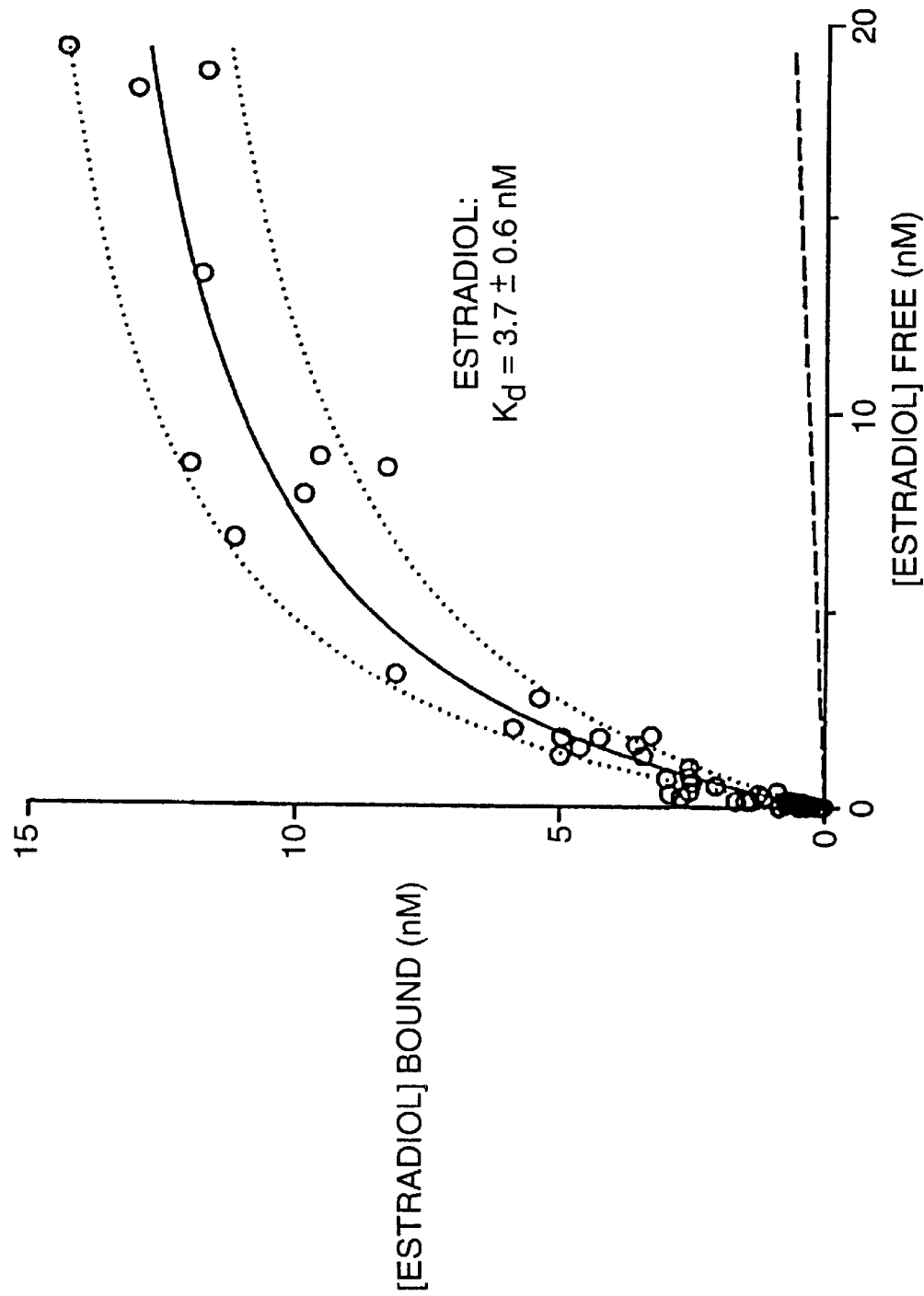
FIG. 3(a) shows specific binding of tritium labelled estradiol to antibody D12; the dashed line shows non-specific binding of an irrelevant (anti-protein) antibody. Antibody diluted 4-fold to 200-fold was incubated with 50 pM tritium labelled estradiol plus unlabelled estradiol giving total estradiol concentrations from 100 pM to 100 $\mu$M. This shows pooled data from 9 experiments. Equilibrium dialysis was carried out for 20 hr at 22° C. in phosphate buffered saline with a membrane having a 12 kDa exclusion limit.

This describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organisation of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate. This application is concerned with antigen-antibody type reactions.

Antibody

This describes an immunoglobulin whether natural or partly or wholly synthetically produced. The term also covers any polypeptide or protein having a binding domain which is, or is homologous to, an antibody binding domain. These can be derived from natural sources, or they may be partly or wholly synthetically produced. Examples of antibodies are the immunoglobulin isotypes and their isotypic subclasses; fragments which comprise an antigen binding domain such as Fab, scFv, Fv, dAh, Fd; and diabodies.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544–546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423–426, 1988; Huston et al, PNAS USA, 85, 5879–5883, 1988); (viii) bispecific single chain Fv dimers (PCT/US92/09965) and (ix) "diabodies", multivalent or multispecific fragments constructed by gene fusion (WO94/13804; P. Holliger et al Proc. Natl. Acad. Sci. USA 90 6444–6448, 1993).

Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804).

Where bispecific antibodies are to be used, these may be conventional bispecific antibodies, which can be manufactured in a variety of ways (Holliger, P. and Winter G. Current Opinion Biotechnol. 4, 446–449 (1993)), eg prepared chemically or from hybrid hybridomas, or may be any of the bispecific antibody fragments mentioned above. It may be preferable to use scFv dimers or diabodies rather than whole antibodies. Diabodies and scFv can be constructed without an Fc region, using only variable domains, potentially reducing the effects of anti-idiotypic reaction. Other forms of bispecific antibodies include the single chain "Janusins" described in Traunecker et al, Embo Journal, 10, 3655–3659, (1991).

Bispecific diabodies, as opposed to bispecific whole antibodies, may also be particularly useful because they can be readily constructed and expressed in E. coli. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected.

Antigen binding domain

This describes the part of an antibody which comprises the area which specifically binds to and is complementary to part or all of an antigen. Where an antigen is large, an antibody may only bind to a particular part of the antigen, which part is termed an epitope. An antibody binding domain may be provided by one or more antibody variable domains. Preferably, an antigen binding domain comprises both an antibody light chain variable region (VL) and an antibody heavy chain variable region (VH), though an antigen binding domain may comprise an antibody heavy chain variable domain or an antibody light chain variable domain, preferably, if only one is to be included, a heavy chain variable domain.

Specific

This may be used to refer to the situation in which one member of a specific binding pair will not show any significant binding to molecules other than its specific binding partner(s). The term is also applicable where e.g. an antigen binding domain is specific for a particular epitope which is carried by a number of antigens, in which case the specific binding member carrying the antigen binding domain will be able to bind to the various antigens carrying the epitope.

Functionally equivalent variant form

This refers to a molecule (the variant) which although having structural differences to another molecule (the parent) retains some significant homology and also at least some of the biological function of the parent molecule, e.g. the ability to bind a particular antigen or epitope. Variants may be in the form of fragments, derivatives or mutants. A variant, derivative or mutant may be obtained by modification of the parent molecule by the addition, deletion, substitution or insertion of one or more amino acids, or by the linkage of another molecule. These changes may be made at the nucleotide or protein level. For example, the encoded polypeptide may be a Fab fragment which is then linked to an Fc tail from another source. Alternatively, a marker such as an enzyme, flourescein, etc, may be linked.

In one aspect, the present invention generally provides a specific binding member comprising a polypeptide which comprises an antibody antigen binding domain which has a dissociation constant of better (i.e. less) than $1.0 \times 10^{-8}$M for estradiol, and a dissociation constant of at least 500 fold worse (i.e. higher) ($1.0 \times 10^{-5}$M) for all other steroid hormones selected from the group consisting of estriol, testosterone, dihydrotestosterone, progesterone, estriol-3-sulphate and estriol 3-β-di-glucuronide. Preferably the dissociation constant is at least 1000 better for estradiol than said other steroid hormones.

A specific binding member comprising an antibody antigen binding domain specific for estradiol wherein the binding domain has a dissociation constant of less than $1.0 \times 10^{-8}$M may comprise any VH or VL domain selected from the VH and VL domains of D12, 1C, 2 Da or 2 Db and 2G, whose sequences are shown in SEQ ID NOs:1–10 (VH domains) and SEQ ID NOs:11–16 (VL domains). In preferred embodiments, the antibody antigen binding domain contains a pairing of VH and VL domains selected from:

(1) the VH domain of D12, the amino acid sequence of which is shown in SEQ ID NO:2 and the VL domain of D12 the amino acid sequence of which is shown in SEQ ID NO:12;

(2) the VH domain of D12, the amino acid sequence of which is shown in SEQ ID NO:2 and a VL domain selected from clone 1C, clone 2D and clone 2G the amino acid sequences of which are shown as SEQ ID NOs:14 (1C/2D) and 16 (2G);

(3) the VL domain of D12 the amino acid sequence of which is shown in SEQ ID NO:12 and a VH domain selected from clone 1C, clone 2G, clone 2Da and clone 2 Db the amino acid sequences of which are shown in SEQ ID NOs:4, 6, 8 and 10 respectively;

(4) a VH domain selected from clone 1C, clone 2G, clone 2 Da and clone 2 Db the amino acid sequences of which are shown as SEQ ID NOs:4, 6, 8 and 10 respectively and a VL domain selected from clone 1C, clone 2D and clone 2G the amino acid sequences of which are shown as SEQ ID NOs:14 (1C/2D) and 16 (2G).

A particularly preferred specific binding member according to the present invention has an antibody antigen binding site formed by association of the VH and VL domains of D12, whose sequences are shown as SEQ ID NO:2 and SEQ ID NO:12 respectively. Such a pairing, in a single-chain Fv molecule, is exemplified and investigated experimentally in Example 3.

The specific binding member may be in the form of an antibody fragment such as single chain Fv (scFv). Other types of antibody fragments may also be utilised such as Fab, Fab', F(ab')2, Fabc, Facb or a diabody (G. Winter and C. Milstein Nature 349, 293–299,1991; WO94/13804). The specific binding member may be in the form of a whole antibody. The whole antibody may be in any of the forms of the antibody isotypes eg IgG, IgA, IgD, IgE and IgM and any of the forms of the isotype subclasses eg IgG1 or IgG4.

The specific binding member may also be in the form of an engineered antibody e.g. a bispecific antibody molecule (or a fragment such as F(ab')2) which has one antigen binding arm (i.e. specific domain) against estradiol and another arm against a different specificity, or a bivalent or multivalent molecule.

In addition to antibody sequences, the specific binding member may comprise other amino acids, e.g. forming a peptide or polypeptide, or to impart to the molecule another functional characteristic in addition to ability to bind antigen. For example, the specific binding member may comprise a label, an enzyme or a fragment thereof and so on.

The binding domain may comprise part or all of a VH domain encoded by a germ line segment or a re-arranged gene segment. The binding domain may comprise part or all of a VL kappa domain or a VL lambda domain.

The binding domain may comprise a VH3 gene sequence of the DP47 germ line or the DP31 germ line; or a re-arranged form thereof. The "DP" nomenclature is described in Tomlinson I. M. et al, (1992) J. Mol. Biol. 227: 776–798.

The binding domain may comprise a V1 2 gene sequence of the germ line DPL11 or a Vk1 gene sequence of the germ line DPK5; or a re-arranged form thereof.

The binding domain may comprise part or all of a VH domain having an amino acid sequence as shown in any one of SEQ ID NOs: 2, 4, 6, 8 or 10 or a functionally equivalent variant form of the said amino acid sequence. Variants are encompassed which differ from the sequences shown by the addition, deletion, substitution or insertion of one or more amino acids and which retain ability to bind estradiol with any of the characteristics for the specific binding members of the present invention as disclosed herein.

The binding domain may comprise part or all of a VL domain having an amino acid sequence as shown in any one of SEQ ID NOs: 12, 14 or 16 or a functionally equivalent variant form of the said amino acid sequence, in the same terms as discussed in the preceding paragraph for VH domains.

The binding domain may comprise one or more CDR (complementarity determining region) with an amino acid sequence of the CDR sequences from SEQ ID NOs:2, 4, 6, 8 or 10 wherein the locations of the CDRs are as shown in FIG. 1(a), as a CDR1, CDR2 or CDR3. In a preferred embodiment, the binding domain comprises a CDR3 sequence shown in FIG. 1(a). Functionally equivalent forms of the CDRs are encompassed by the present invention. Variants are encompassed that differ from the sequences shown by the addition, deletion, substitution and/or insertion of one or more amino acids and which retain ability to bind estradiol with one or more of the characteristics for the specific binding members of the present invention as disclosed herein. The specific binding member may comprise all or part of the framework regions flanking and between the CDRs or different framework regions including modified versions of those shown. These frameworks may or may not be used with one or more of the CDR sequences from the clones D12 (SEQ ID NOs:2 and 12), 1C (SEQ ID NOs:4 and 14), 2Da (SEQ ID NOs:8 and 14) or 2G (SEQ ID NOs:6 and 16). Particular variants may include one or more amino acid sequence alterations (addition, deletion, substitution and/or insertion of an amino acid), maybe less than about 25 alterations, less than about 20 alterations, less than about 15 alterations, less than about 10 alterations or less than about 5 alterations, 4, 3, 2 or 1. Alterations may be made in one or more framework regions and/or one or more CDR's.

The binding domain may comprise one or more CDR (complementarity determining region) with an amino acid sequence of the CDR sequences from SEQ ID NOs:12, 14 or 16 wherein the locations of the CDRs are as shown in FIG. 1(b), as a CDR1, CDR2 or CDR3. In a preferred embodiment, the binding domain comprises a CDR3 sequence shown in FIG. 1(b). Functionally equivalent variant forms of the CDRs are encompassed by the present invention, in particular variants which differ from the CDR sequences shown by addition, deletion, substitution and/or insertion of one or more amino acids and which retain ability to bind estradiol and optionally one or more of the preferred characteristics for specific binding members of the present invention as disclosed herein. The specific binding member may comprise all or part of the framework regions shown flanking and between the CDRs in FIG. 1(b), or different framework regions including modified versions of those shown.

So-called "CDR-grafting" in which one or more CDR sequences of a first antibody is placed within a framework of sequences not of that antibody, e.g. of another antibody, is disclosed in EP-B-0239400, which has an equivalent U.S. patent.

A specific binding member according to the invention may be one which competes with any specific binding member which binds estradiol and comprises part of all of any of the sequences shown as SEQ ID NOs:2, 4, 6, 8 or 10, or as SEQ ID NOs:12, 14 or 16. For example, such a specific binding member may compete with D12 for binding to estradiol. Competition between binding members may be assayed easily in vitro, for example by tagging a specific reporter molecule to one binding member which can be detected in the presence of other untagged binding member (s), to enable identification of specific binding members which bind the same epitope or an overlapping epitope.

Specific binding members according to the invention may be provided in isolated and/or purified form.

The present invention provides the use of a specific binding member as above in monitoring estradiol levels, for instance during the menstrual cycle, in hormone replacement therapy and for diagnosing estrogen secreting tumours.

This may be performed in vivo or in vitro on a test sample of material such as a body fluid, e.g. blood or urine, removed from the body.

The present invention provides a method comprising causing or allowing binding of a specific binding member as as provided herein to estradiol. Such binding may take place in vitro or in vivo. The amount of binding of specific binding member to estradiol may be determined. Quantitation may be related to the amount of estradiol in a test sample, which may be of diagnostic interest.

The reactivities of antibodies on a sample may be determined by any appropriate means. Radioimmunoassay (RIA) is one possibility. Radioactive labelled estradiol is mixed with unlabelled estradiol (the test sample) and allowed to bind to the antibody. Bound estradiol is physically separated from unbound estradiol and the amount of radioactive estradiol bound to the antibody determined. The more estradiol there is in the test sample the less radioactive estradiol will bind to the antibody. A competitive binding assay may also be used with non-radioactive estradiol, using estradiol or an analogue of estradiol linked to a reporter molecule. The reporter molecule may be a fluorochrome, phosphor or laser dye with spectrally isolated absorption or emission characteristics. Suitable fluorochromes include afluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The signals generated by individual antibody-reporter conjugates may be used to derive quantifiable absolute or relative data of the relevant antibody binding in samples (normal and test).

The present invention also provides the use of a specific binding member as above for measuring estradiol levels in a competition assay, that is to say a method of measuring the level of estradiol in a sample by employing a specific binding member as provided by the present invention in a competition assay. This may be where the physical separation of bound from unbound estradiol is not required. Linking a reporter molecule to the specific binding member so that a physical or optical change occurs on binding is one possibility. The reporter molecule may directly or indirectly generate detectable, and preferably measurable, signals. The linkage of reporter molecules may be directly or indirectly, covalently, eg via a peptide bond or non-covalently. Linkage via a peptide bond may be as a result of recombinant expression of a gene fusion encoding antibody and reporter molecule.

The present invention also provides for measuring levels of estradiol directly, by employing a specific binding member according to the invention for example in a biosensor system.

The mode of determining binding is not a feature of the present invention and those skilled in the art are able to choose a suitable mode according to their preference and general knowledge.

A specific binding member according to the present invention may be made by expression from encoding nucleic acid. Nucleic acid encoding any specific binding member as provided itself forms an aspect of the present invention, as does a method of production of the specific binding member which method comprises expression from encoding nucleic acid therefor. Expression may conveniently be achieved by culturing under appropriate conditions recombinant host cells containing the nucleic acid.

The nucleic acid may encode any of the amino acid sequences shown as SEQ ID NOs:2, 4, 6, 8 or 10 and SEQ ID NOs:12, 14 or 16, or any functionally equivalent form. The nucleotide sequences employed may be any of those shown as SEQ ID NOs:1, 3, 5, 7 or 9 or SEQ ID NOs: 11, 13 or 15 or may be a variant, allele or derivative thereof. Changes may be made at the nucleotide level by addition, substitution, deletion and/or insertion of one or more nucleotides, which changes may or may not be reflected at the amino acid level, dependent on the degeneracy of the genetic code.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells and many others. A common, preferred bacterial host is *E. coli*.

The expression of antibodies and antibody fragments in prokaryotic cells such as E. coli is well established in the art. For a review, see for example Pluckthun, A. Bio/Technology 9: 545–551 (1991). Expression in eukaryotic cells in culture is also available to those skilled in the art as an option for production of a specific binding member, see for recent reviews, for example Reff, M. E. (1993) Curr. Opinion Biotech. 4: 573–576; Trill J. J. et al. (1995) Curr. Opinion Biotech 6: 553–560.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, *Molecular Cloning: a Laboratory Manual:* 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Short Protocols in Molecular Biology*, Second Edition, Ausubel et al. eds., John Wiley & Sons, 1992. The disclosures of Sambrook et al. and Ausubel et al. are incorporated herein by reference.

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene.

In one embodiment, the nucleic acid of the invention is integrated into the genome (e.g. chromosome) of the host cell. Integration may be promoted by inclusion of sequences which promote recombination with the genome, in accordance with standard techniques.

Following production of a specific binding member it may be used for example in any of the manners disclosed herein, such as in the formulation of a composition such as a pharmaceutical, or a diagnostic product, such as a kit comprising in addition to the specific binding member one or more reagents for determining binding of the member to cells, as discussed.

Further aspects of the invention and embodiments will be apparent to those skilled in the art. In order that the present invention is fully understood, the following examples are provided by way of exemplification only and not by way of limitation. Reference is made to the following figures:

All documents mentioned herein are incorporated by reference. The term "comprising" as used herein permits the inclusion of additional features or components.

In the work described herein, methods were optimised to select highly specific estradiol-binding antibodies from a repertoire of single-chain Fv (scFv) antibodies from non-immunised humans. Screening by ELISA for clones whose binding to BSA-estradiol can be inhibited by free estradiol in solution favours the isolation of antibodies with high specificity for estradiol and low cross-reactivity with related steroids. This results in clones with high affinity and reduces loss in specificity for that end of the estradiol molecule by which it was conjugated to BSA.

Figure 3B:
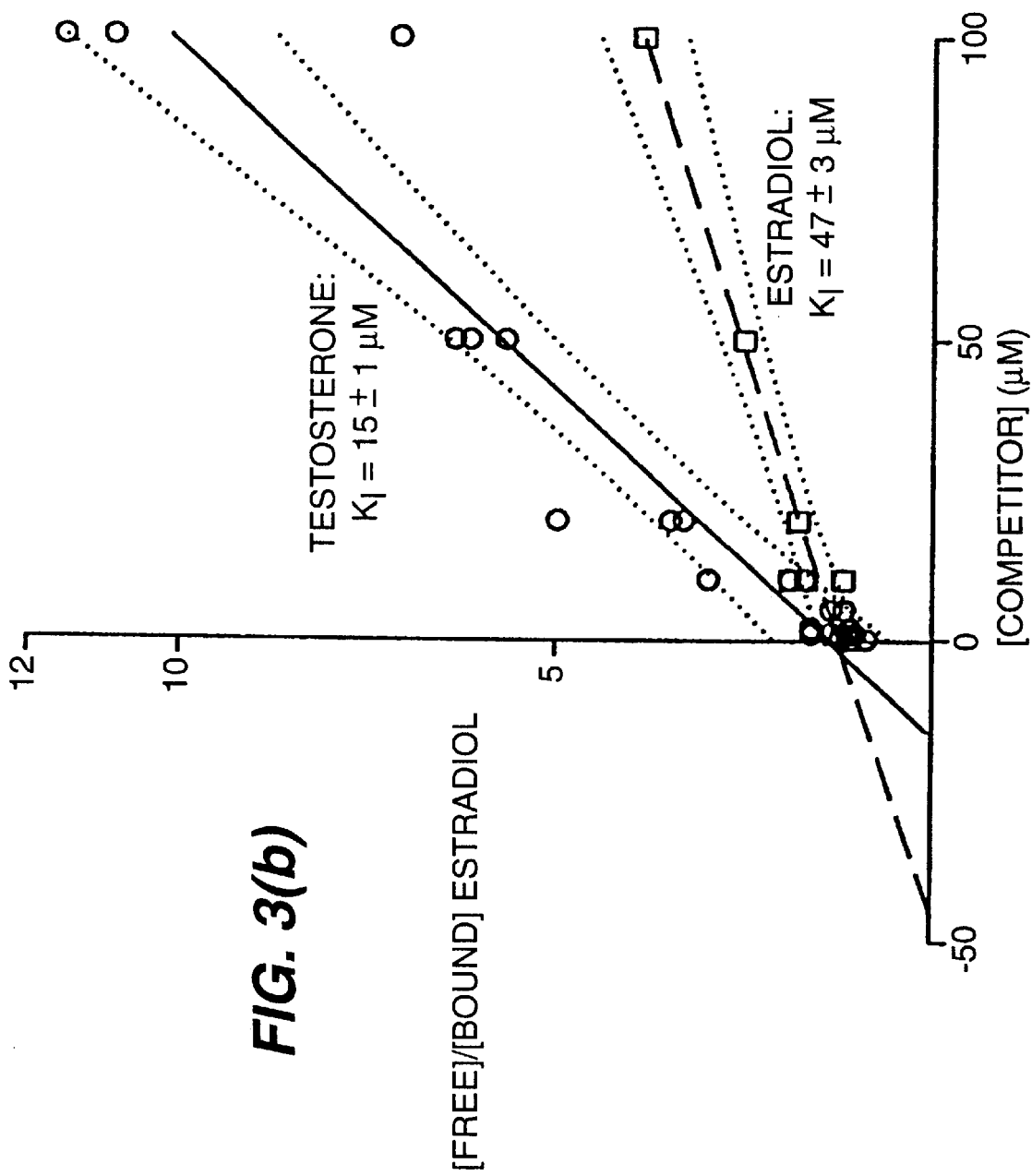
FIG. 3(b) shows testosterone or estradiol competition with tritium labelled estradiol for specific binding to antibody D12. Antibody D12 (13.3 nM) was incubated with 4 nM tritium labelled estradiol, plus competing steroid (100 nM to 100 $\mu$M). Pooled data from 3 experiments. Equilibrium dialysis was carried out for 20 hr at 22° C. in phosphate buffered saline with a membrane having a 12 kDa exclusion limit.

Various embodiments of resulting antibodies bind estradiol with a dissociation constant for estradiol of 3.7 nM (FIG. 2) as determined by equilibrium dialysis (FIG. 3). Affinities for other steroids were determined by methods using soluble, unmodified steroid.

The primary screen was an ELISA based technique measuring inhibition of antibody binding to BSA-estradiol by soluble steroid. Estriol-3-β-D-glucuronide and cholesterol did not show any inhibition of binding of the antibody to BSA-estradiol. 5 Estriol-3 sulphate, 16-epiestriol 17-epiestriol and progesterone inhibited only at very high concentrations (100 μM). Testosterone and dihydrotestosterone showed inhibition of binding to BSA-estradiol at 30 μM. This ELISA based screening method therefore demonstrated that antibody had good specificity for estradiol.

Affinities for testosterone, dihydrotestosterone, estriol, 16-epiestriol and estriol-3 sulphate were then measured accurately by equilibrium dialysis. This showed that the affinities for these cross-reactive structures range from 15 mM for testosterone to 163 mM for 16-epiestriol (FIG. 2). Hence, in addition to its high affinity, the antibody also has excellent selectivity.

EXAMPLE 1

Identification and characterisation of antibodies to estradiol by selection of an unimmunised phage antibody repertoire Antigen Estradiol (1,3,5.estratriene 3,17 β-diol ), BSA-estradiol and BSA-progesterone were supplied by Steraloids, $^3$H labelled estradiol (5.2 TBq/mM) by Amersham. All other steroids were supplied by Sigma. Thyroglobulin-estradiol was prepared by linking 6-carboxy methyl oxime (CMO) estradiol (Sigma) covalently to bovine thyroglobulin using standard methods [Cook, B. & Beastall, G.(1989)], and was purified by gel filtration.

Antibody repertoire

The following antibody repertoire was used:

Large single chain Fv library derived from lymphoid tissues including tonsil, bone marrow and peripheral blood lymphocytes.

Polyadenylated RNA was prepared from the B-cells of various lymphoid tissues of 43 non-immunised donors using the "Quickprep mRNA Kit" (Pharmacia). First-strand cDNA was synthesized from mRNA using a "First-strand cDNA synthesis" kit (Pharmacia) using random hexamers to prime synthesis. V-genes were amplified using family-specific primers for VH, Vk and Vl genes as previously described (Marks et al. (1991) J.Mol.Biol. 222 581–597) and subsequently recombined together with the $(Gly_4, Ser)_3$ scFv linker by PCR assembly. The VH-linker-VL antibody constructs were cloned into the Sfi I and Not I sites of the phagemid vector, pCANTAB 6. Ligation, electroporation and plating out of the cells was as described previously (Marks et al, supra).

The library was made ca. 1000× larger than that described previously by bulking up the amounts of vector and insert used and by performing multiple electroporations. This generated a scFv repertoire that was calculated to have ca. $1.3 \times 10^{10}$ individual recombinants which by Bst NI fingerprinting were shown to be extremely diverse.

a. Induction of phage antibody library

The phage antibody repertoire above was selected for antibodies to estradiol. The 'large' scFv repertoire was treated as follows in order to rescue phagemid particles. 500 ml prewarmed (37° C.) 2YTAG (2YT media supplemented with 100 µg/ml ampicillin and 2% glucose) in a 2 l conical flask was inoculated with approximately $3 \times 10^{10}$ cells from a glycerol stock (−70° C.) culture of the library. The culture was grown at 37° C. with good aeration until the OD600 nm reached 0.7 (approximately 2 hours). M13K07 helper phage (Stratagene) was added to the culture to a multiplicity of infection (moi) of approximately 10 (assuming that an $OD_{600\ nm}$ of 1 is equivalent to $5 \times 10^8$ cells per ml of culture). The culture was incubated stationary at 37° C. for 15 minutes followed by 45 minutes with light aeration (200 rpm) at the same temperature. The culture was centrifuged and the supernatant drained from the cell pellet. The cells were resuspended in 500 ml 2YTAK (2YT media supplemented with 100 µg/ml ampicillin and 50 µg/ml kanamycin), and the culture incubated overnight at 30° C. with good aeration (300 rpm). Phage particles were purified and concentrated by three polyethylene glycol (PEG) precipitations (Sambrook, J., Fritsch, E. F., & Maniatis, T. (1990). Molecular Cloning—A Laboratory Manual. Cold Spring Harbour, N.Y.) and resuspended in PBS to $10^{12}$ transducing units (tu)/ml (ampicillin resistant clones).

b. Panning of phage antibody library on BSA-estradiol

Phage induced from the repertoire was panned on BSA-estradiol. A 75 mm×12 mm immuno tube (Nunc; Maxisorp) was coated with 1 ml of BSA-estradiol (5 ug/ml) in PBS overnight at room temperature.

(BSA-estradiol supplied by Steraloids with 30 to 40 estradiol molecules conjugated to each BSA molecule) After washing 3 times with PBS, the tube was filled with 2% MPBS (2% 'Marvel' skimmed milk powder, 1× PBS) and incubated for 2 hours at 37° C. for blocking. The wash was repeated, phagemid particles ($10^{13}$ tu) in 1 ml of 2% MPBS were added and the tube incubated stationary at 37° C. for 1 hour. The tube was washed 20 times with PBST (PBS with 0.1% TWEEN), then 20 times with PBS. Bound phage particles were eluted from the tube by adding 1 ml of 100 mM-triethylamine, and incubating the tube stationary at room temperature for 10 minutes. The eluted material was immediately neutralised by pipetting into a tube containing 0.5 ml 1M-Tris.HCl (pH7.4). The eluted phage were immediately used to infect 10 ml of logarithmically growing *E. coli* TG1 (Gibson, T. J. (1984). PhD thesis. University of Cambridge, UK.). Infected cells were grown for 1 hour at 37° C. with light aeration in 2YT broth, and then plated on 2YTAG medium in 243 mm×243 mm dishes (Nunc). Plates were incubated overnight at 30° C. Colonies were scraped off the plates into 10 ml of 2YT broth and 15% (v/v) glycerol added for storage at −70° C.

Glycerol stock cultures from the first round of panning the repertoire on BSA-estradiol were rescued using helper phage to derive phagemid particles for the second round of panning. 250 µl of glycerol stock was used to inoculate 50 ml 2YTAG broth, and incubated in a 250 mL conical flask at 37° C. with good aeration until the $OD_{600\ nM}$ reached 0.7 (approximately 2 hours). M13K07 helper phage (moi=10) was added to the culture which was then incubated at 37° C. for 60 minutes with light aeration (120 rpm). The culture was centrifuged and the supernatant drained from the cell pellet. The cells were resuspended in 50 ml prewarmed 2YTAK, and the culture incubated overnight at 30° C. with good aeration (300 rpm). This overnight growth gives phage particles suitable for the next round of selection. All cells were removed by centrifugation and the resulting supernatant of phage particles was used immediately in the next round of selection.

Phage induced from the first round of panning the repertoire was selected a second time as described above. The process of phage growth and panning was then repeated for a third round of selection.

c. Growth of single selected clones for immunoassay

Individual colonies from the second and third round selections were used to inoculate 100 µl 2YTAG into individual wells of 96 well tissue culture plates (Corning). Plates were incubated at 30° C. overnight with moderate shaking (100 rpm). Glycerol to 15% was added to each well and these master plates stored at −70° C. until ready for analysis.

d. ELISA to identify anti-estradiol scFv

Clones specific for estradiol were identified by ELISA, using scFv displayed on phage or soluble scFv.

(i) Phage ELISA

Cells from the master plates were used to inoculate fresh 96 well tissue culture plates containing 100 µl 2YTAG per well. These plates were incubated at 37° C. for 6–8 hours or until the cells in the wells were growing logarithmically (OD600 0.2–1.0). M13K07 was added to each well to an moi of 10 and incubated stationary for 15 min then 45 min with gentle shaking (100 rpm), both at 37° C. The plates were centrifuged at 2000 rpm for 10 min and the supernatant eluted. Each cell pellet was resuspended in 100 µl 2YTAK and incubated at 30° C. overnight.

Each plate was centrifuged at 2000 rpm and the 100 µl supernatant from each well recovered and mixed with 100 µl 4%M-2PBS (4% skimmed milk powder, 2× PBS), stationary at room temperature for 1 hour. Meanwhile, flexible microtitre plates which had been coated overnight stationary at room temperature with either 100 µl 5 µg/ml BSA-estradiol in PBS or 100 µl PBS alone (giving an uncoated control plate), were washed 3 times in PBS and blocked for 2 h stationary at 37° C. in 2% MPBS (2% skimmed milk powder in PBS). These plates were then washed three times with PBS and 90 µl preblocked phage added to each well of both the BSA-estradiol coated or uncoated plate. The plates were incubated stationary at room temperature for 1 h after which the phage were poured off. The plates were washed by incubating for 2 min in PBST three times followed by incubating for 2 min in PBS three times, all at room temperature.

To each well of both the BSA-estradiol coated and the uncoated plate, 90 µl of a 1 in 10000 dilution of sheep anti-fd antibody (Pharmacia) in 2% MPBS was added and the plates incubated at room temperature for 1 h. Each plate was washed as described above and 90 µl of a 1 in 5000 dilution donkey anti-sheep alkaline phosphatase conjugate (Sigma) in 2% MPBS added and incubated stationary for 1 h. Plates were washed as described as above followed by two rinses in 0.9% NaCl. Alkaline phosphatase activity was visualised using the chromagenic substrate pNPP (p-Nitrophenylphosphate) (Sigma). The absorbance signal generated by each clone was assessed by measuring the optical density at 405 nm using a microtitre plate reader.

Clones were chosen for further analysis if the ELISA signal generated on the BSA-estradiol coated plate was significantly above background. None of the clones gave a signal on the uncoated plate.

(ii) Soluble ELISA

Cells from the master plates were used to inoculate fresh 96 well tissue culture plates containing 100 µl 2YTAG per well. These plates were incubated at 30° C. for 8 hours then centrifuged at 2000 rpm for 10 min and the supernatant eluted. Each cell pellet was resuspended in 100 μl 2YTA containing 1 mM IPTG and incubated at 30° C. overnight.

Each plate was centrifuged at 2000 rpm and the 100 μl supernatant from each well recovered and mixed with 100 μl 4%M-2PBS (4% skimmed milk powder, 2× PBS), stationary at room temperature for 1 hour. Meanwhile, flexible microtitre plates which had been coated overnight stationary at room temperature with either 100 μl 5 μg/ml BSA-estradiol in PBS or 100 μl PBS alone (giving an uncoated control plate), were washed 3 times in PBS and blocked for 2 h stationary at 37° C. in 2% MPBS. These plates were then washed three times with PBS and 90 μl preblocked culture supernatant added to each well of both the BSA-estradiol coated or uncoated plate. The plates were incubated stationary at room temperature for 1 h after which the culture supernatants were poured off. The plates were washed by incubating for 2 min in PBST three times followed by incubating for 2 min in PBS three times, all at room temperature.

To each well of both the BSA-estradiol coated and the uncoated plate, 90 μl of a 1 in 200 dilution of the anti-myc tag murine antibody 9 μl (Munro, S. & Pelham, H. R. B. (1986)Cell 46, 291–300) in 2% MPBS was added and the plates incubated at room temperature for 1 h. Each plate was washed as described above and 90 μl of a 1 in 5000 dilution goat anti-mouse alkaline phosphatase conjugate (Pierce) in 2% MPBS added and incubated stationary at 37° C. for 1 h. Plates were washed as described above followed by two rinses in 0.9% NaCl. Alkaline phosphatase activity was visualised using the chromagenic substrate pNPP (Sigma). The absorbance signal generated by each clone was assessed by measuring the optical density at 405 nm using a microtitre plate reader.

Clones were chosen for further analysis if the ELISA signal generated on the BSA-estradiol coated plate was significantly above background. None of the cultures gave a signal on the uncoated plate.

EXAMPLE 2

Demonstration of binding of antibodies specific for estradiol a. Specificity ELISA A panel of 128 estradiol binding clones was picked from the second and third rounds of selection and tested for specificity by ELISA.

Specificity ELISA's were carried out using scFv either displayed on phage or in solution as described above, except that 5 ml of media in 50 ml Falcon tubes were inoculated with each clone and grown to generate the phage or soluble scFv used in the ELISA. Microtitre plate wells were coated with 100 μl of either 5 μg/ml BSA-estradiol, 5 μg/ml thyroglobulin-estradiol, 5 μg/ml bovine serum albumin (BSA), 5 μg/ml BSA-estriol, or 5 μg/ml BSA-progesterone. The phage (or soluble scFv) and the microtitre plates were preblocked with 2% MPBS. 50 μl of blocked phage (or soluble scFv) from each clone was then added to a well coated with either BSA-estradiol, thyroglobulin-estradiol, bovine serum albumin (BSA), BSA-estriol, or BSA-progesterone. As above, alkaline phosphatase activity was visualised using the chromagenic substrate pNPP (Sigma).

None of the 128 selected clones bound to BSA, BSA-oestriol, BSA-progesterone or an uncoated ELISA plate. Of these, 75 appeared to be estradiol-specific in that they bound both thyroglobulin-estradiol and BSA-estradiol. We assume that the remaining clones recognise BSA-estradiol but not free estradiol.

b. Screening selected clones for high affinity

An ELISA-based screening method was used to rank different clones on the basis of their relative equilibrium dissociation constants for estradiol. In this assay, crude culture supernatant was equilibrated with soluble steroids at a range of concentrations (10 μM, 1 μM, 100 nM and zero estradiol) then applied to ELISA wells coated with estradiol-ESA. Affinity for the soluble steroid was then indicated by a reduction in ELISA signal intensity due to the antibody being in complex with the soluble ligand and unavailable for binding to the plate. This gives a reduction in ELISA signal. Clones with highest affinity for estradiol were those exhibiting the greatest signal reduction with the lowest concentrations of free estradiol.

This assay was used to rank clones on the basis of affinity for free estradiol. This screening test also ensured that only those antibodies binding to unmodified estradiol were taken for further analysis. This screening is important for the selection of clones with a high affinity for free estradiol and should consequently select those clones with good specificity for estradiol and a low affinity for related steroids.

Of the 75 clones analysed, the top 8 were chosen for detailed investigation.

c. Sequencing of estradiol-Specific ScFv Antibodies

The 8 clones chosen for detailed investigation were sequenced. Vector-specific primers were used to amplify the inserted DNA from each clone. Cells from an individual colony on a 2YTAG agar plate were used as the template for a polymerase chain reaction (PCR) amplification of the inserted DNA using the primers pUC19reverse (SEQ ID NO:20) and fdtetseq (SEQ ID NO:19). Amplification conditions consisted of 30 cycles of 94° C. for 1 min, 55° C for 1 min and 72° C. for 2 min, followed by 10 min at 72° C. The PCR products were purified using a PCR Clean-up Kit (Promega) in to a final volume of 50 μl $H_2O$. Between 2 and 5 μl of each insert preparation was used as the template for sequencing using the Taq Dye-terminator cycle sequencing system (Applied Biosystems). The primers mycseqlo (SEQ ID NO:21) and PCR-L-Link (SEQ ID NO:22) were used to sequence the light chain of each clone and PCR-H-Link (SEQ ID NO:21) and pUC19reverse (SEQ ID NO:20) to sequence the heavy chain.

Of the 8 clones sequenced, 6 had identical DNA sequences represented by clone 1C (SEQ ID NOs:4 and 12, and FIG. 1). This clone utilised a DP47 heavy chain germline sequence and a DP11 lambda light chain and was present in both the panned and solution-capture populations. Clone 2 Da(SEQ ID NOs:8 and 12) used a heavy chain derived from a different germline (DP31) but retained the same DP11 light chain. In another aspect of the invention, the N-terminal residue of clone 2 Da may be altered to glutamic acid, in keeping with the N-terminii of the other sequences shown as FIG. 1a (The alteration may be effected using standard techniques such as site directed mutagenesis of a clone comprising SEQ ID NO:7 to provide a clone comprising the sequence of SEQ ID NO:9, and expressing said SEQ ID NO:9). Clone 2G (SEQ ID NOs:6 and 16) was derived from the same DP47 germline as clone 1C but with a different VH CDR3 sequence and its light chain partner was a kappa light chain from the DPK5 germline. This clone ranked lower than the others in that it exhibited lower inhibition of binding with soluble estradiol.

d. Affinity maturation

Both heavy and light chains of the selected clones were shuffled with V genes from non-immunized donors in an attempt to increase the affinity of the primary antibodies (Clackson et al. (1991) Nature 352 624–628). The resulting clones were selected by panning on BSA-estradiol as described in example 1. These were then screened as described in example 2(b).

In each case, sequences highly homologous or identical to class 1C were selected. These observations underline the gene preference of the estradiol antibodies. The highest-ranking clone in ELISA was designated D12 (SEQ ID NOs:2 and 12), and appeared to have a higher affinity for estradiol than parental clone 1C. This clone was identical to class 1C antibodies apart from a single point mutation (Ala80–Val80 by the Kabat numbering system (Kabat et al. (1991) Sequences of proteins of immunological interest. NIH publication No 91-3242) in the lambda light chain, which appears to have resulted from a PCR error during the chain shuffle. The binding properties of this antibody were then analysed in detail.

EXAMPLE 3

Preparation and characterisation of antibody D12 a. Preparation and purification of scFv antibody.

The estradiol binding clone D12 was cloned into the phagemid vector pUC119Sfi [whose polylinker region is shown as SEQ ID NO:17 and as FIG. 4] in *Escherichia coli* TG1 cells, and the scFv purified by metal chelate chromatography (Qiagen) according to the manufacturer's instructions. Approximately 3 mg of purified antibody per liter of cells was routinely recovered with this affinity purification method. Purity was estimated to be approximately 50% as assessed by silver staining on SDS-PAGE. Purified antibody preparations were stored as frozen aliquots at −70° C.

b. Determination of affinities and kinetics of steroid binding to antibody D12

Equilibrium dialysis was carried out at 22° C. in phosphate-buffered saline (PBS) using a microdialyzer (Hoefer) with a membrane having a 12 kDa exclusion limit. Dialysis of 100 nM estradiol in the absence of antibody demonstrated that equilibrium was achieved after overnight incubation. Antibody diluted 4-fold to 200-fold (from 0.7 nM to 33 nM, based on concentrations calculated from binding data) was incubated with 50 pM labelled estradiol (Amersham, tritium-labelled at positions 2,4,6,7,16,17) plus unlabelled estradiol to give total estradiol concentrations from 100 pM–100 $\mu$M. Mixtures were equilibrated for 2 h at 22° C. and dialysed against PBS for 20 h with constant mixing, before taking samples from each chamber for measurement of radioactivity. Addition of radiolabelled estradiol to either the antibody-containing compartment or the compartment without antibody resulted in the same equilibrium distribution of radioactivity between the compartments. Non-specific binding was quantified by measuring non-saturable binding of 1–200 $\mu$M estradiol to the D12 antibody preparation, and by measuring estradiol binding to a comparable preparation of a different scFv that had been selected against an irrelevant protein antigen.

Over the range of ligand concentrations necessary for affinity measurement (up to 100 nM), less than 10% of labelled estradiol bound non-specifically. After subtraction of non-specific binding, the dissociation constant (Kd) of estradiol binding to antibody D12 was calculated from equilibrium dialysis data using a non-linear least-squares fit, assuming a single class of binding sites.

c. Determination of specificity of estradiol binding by antibody D12

The binding properties of other steroids were investigated by measuring their ability to compete with estradiol for binding to D12 antibody. This was investigated using the ELISA based screening method (Example 2b) and any cross-reacting compounds were investigated further by equilibrium dialysis.

Culture supernatant from the antibody clone D12 was equilibrated with soluble steroid at a range of concentrations from 5 nM to 100 mM (or the limit solubility of the steroid), then transferred to an ELISA plate coated with BSA-estradiol. The ELISA plate was then processed as for a standard phage ELISA assay. Affinity for the soluble competing steroid was then indicated by a reduction in ELISA signal intensity due to the antibody being in complex with the soluble ligand and unavailable for binding to the plate.

The specificity of the antibody D12 for estradiol over other steroids was very high. On ELISA, neither cholesterol nor estriol-3-$\beta$-D-glucuronide inhibited the binding of estradiol to the antibody. Estriol-3-sulphate, 16-epiestriol, 17-epiestriol and progesterone inhibited estradiol binding when present at 100 $\mu$M. Testosterone inhibited estradiol binding when present at 30 $\mu$M. Dihydrotestosterone also inhibited estradiol binding when present at 30 $\mu$M. Estriol was at its solubility limit of 30 $\mu$M and did not inhibit estradiol binding in ELISA, confirming our observation of a complete lack of binding to estriol-BSA in ELISA (Example 2a).

Antibody D12 (at a concentration of 13.3 nM) was incubated for 2 h with a mixture containing both tritium labelled estradiol (4 nM) and the competing steroid (100 nM to 100 $\mu$M), before equilibrium dialysis. The binding of other steroids to D12 antibody was quantified assuming competitive inhibition of estradiol binding. Data was analyzed with proprietary software (FIG.P package: Elsevier Biosoft).

In this way the affinities for testosterone, dihydrotestosterone, estriol, 16-epiestriol and estriol-3 sulphate were measured accurately. The affinities for these cross-reactive structures range from 15 mM for testosterone to 163 mM for 16-epiestriol (FIG. 2). Therefore, in addition to its high affinity, the antibody also has excellent selectivity. This equilibrium dialysis study demonstrated that the antibody had an approximately 1,000—fold selectivity for estradiol over testosterone, which was the most potent competitor (FIG. 3). The antibody bound the other steroids with affinities approximately 5,000-fold weaker than its affinity for estradiol (FIG. 2).

TABLE 1

Oligonucleotide primers used in the identification and characterisation of estradiol antibodies.

| | | |
|---|---|---|
| FDTSEQ: | 5'-GTCGTCTTTCCAGACGTTAGT-3' | SEQ ID NO: 19 |
| pUC19REVERSE: | 5'-AGCGGATAACAATTTCACACAGG-3' | SEQ ID NO: 20 |
| MYCSEQ10: | 5'-CTCTTCTGAGATGAGTTTTTG-3' | SEQ ID NO: 21 |
| PCR-L-LINK: | 5'-GGCGGAGGTGGCTCTGGCGGT-3' | SEQ ID NO: 22 |
| PCR-H-LINK: | 5'-ACGGCCAGAGCCACCTCCGCC-3' | SEQ ID NO: 23 |

Although the foregoing invention has been described in detail by way of illustration and example for purposes of clarity of understanding, it will be readily apparent to those of skill in the art in the light of the teachings of the invention that certain changes and modifications may be made thereto without departing from the spirit or scope of the appended claims, which follow the sequence listing.

What is claimed is:

1. A specific binding member comprising a polypeptide which comprises an antibody antigen binding domain which has a dissociation constant of less than $1.0 \times 10^{-8}$M for estradiol, and a dissociation constant of at least 500 fold higher for the steroid hormones selected from the group consisting of estriol, testosterone, dihydrotestosterone, progesterone, estriol-3-sulphate and estriol 3-β-diglucuronide, wherein said polypeptide comprises an antibody VH domain whose CDRs are of a sequence as shown in the CDRs of the VH domains selected from SEQ ID NO:2, SEQ ID NO:4, SEQ ID NO:6, SEQ ID NO:8 and SEQ ID NO: 10.

2. The specific binding member of claim 1 wherein the dissociation constant is at least 1000 better for estradiol than for said other steroid hormones.

3. The specific binding member of claim 1 wherein said polypeptide further comprises an antibody VL domain whose CDRs are of a sequence as shown in the CDRs of the VL domains selected from SEQ ID NO:12, SEQ ID NO:14 and SEQ ID NO:16.

4. The specific binding member of claim 1 wherein said polypeptide comprises an antibody VH domain whose sequence is selected from SEQ ID NO:2, SEQ ID NO:4, SEQ ID NO:6, SEQ ID NO:8 and SEQ ID NO:10.

5. The specific binding member of claim 4 wherein said polypeptide further comprises an antibody VL domain whose sequence is selected from SEQ ID NO:12, SEQ ID NO:14 and SEQ ID NO:16.

6. The specific binding member of claim 1 which is an antibody fragment selected from the group consisting of scFv, Fab, F(ab') and F(ab')2 fragments.

7. The specific binding member of claim 3 which is an antibody fragment selected from the group consisting of scFv, Fab, F(ab') and F(ab')2 fragments.

8. The specific binding member of claim 5 which is an antibody fragment selected from the group consisting of scFv, Fab, F(ab') and F(ab')2 fragments.

9. The specific binding member of claim 1 which is a whole antibody.

10. The specific binding member of claim 3 which is a whole antibody.

11. The specific binding member of claim 5 which is a whole antibody.

12. An antibody or fragment thereof which comprises an antibody antigen binding domain which has a dissociation constant of less than $1.0 \times 10^{-8}$M for estradiol, wherein said antibody has a VH domain as shown in SEQ ID NO:2 and a VL domain as shown in SEQ ID NO:12.

13. An immunoassay method for determining the presence or absence of estradiol in a sample which comprises:
    a) bringing said sample into contact with a specific binding member comprising a polypeptide which comprises an antibody antigen binding domain which has a dissociation constant of less than $1.0 \times 10^{-8}$M for estradiol, and a dissociation constant of at least 500 fold higher for the steroid hormones selected from the group consisting of estriol, testosterone, dihydrotestosterone, progesterone, estriol-3-sulphate and estriol 3-β-di-glucuronide under conditions which allow binding of estradiol, if present in said sample, to said specific binding member, said polypeptide comprising an antibody VH domain whose CDRs are of a sequence as shown in the CDRs of the VH domains selected from SEQ ID NO:2, SEQ ID NO:4, SEQ ID NO:6, SEQ ID NO:8 and SEQ ID NO: 10.; and b) detecting the binding of said specific binding member to estradiol, if present, in the sample.

14. An assay according to claim 13 which is a competitive assay.

15. An assay according to claim 13 wherein the amount of estradiol in the sample is quantitated.

16. An assay according to claim 13 wherein said sample comprises a urine sample from a human female.

17. An immunoassay method according to claim 13 wherein said polypeptide further comprises an antibody VL domain whose CDRs are of a sequence as shown in the CDRs of the VL domains selected from SEQ ID NO: 12, SEQ ID NO: 14 and SEQ ID NO:16.

18. An immunoassay method according to claim 13 wherein said polypeptide comprises an antibody VH domain whose sequence is selected from SEQ ID NO:2, SEQ ID NO:4, SEQ ID NO:6, SEQ ID NO:8 and SEQ ID NO:10.

19. An immunoassay method according to claim 18 wherein said polypeptide further comprises an antibody VL domain whose sequence is selected from SEQ ID NO: 12, SEQ ID NO: 14 and SEQ ID NO:16.

20. An immunoassay method according to claim 13 wherein said specific binding member is an antibody fragment selected from the group consisting of scFv, Fab, F(ab') and F(ab')2 fragments.

21. An immunoassay method according to claim 13 wherein said specific binding member is a whole antibody.

22. An immunoassay method for determining the presence or absence of estradiol in a sample which comprises:

a) bringing said sample into contact with a specific binding member comprising a polypeptide which comprises an antibody antigen binding domain which has a dissociation constant of less than $1.0 \times 10^{-8}$M for estradiol, and a dissociation constant of at least 500 fold higher for the steroid hormones selected from the group consisting of estriol, testosterone, dihydrotestosterone, progesterone, estriol-3-sulphate and estriol 3-β-di-glucuronide under conditions which allow binding of estradiol, if present in said sample, to said specific binding member, said antibody antigen binding domain comprising a VH domain as shown in SEQ ID NO:2 and a VL domain as shown in SEQ ID NO:12; and b) detecting the binding of said specific binding member to estradiol, if present, in the sample.

* * * * *

SEQUENCE LISTING (1) GENERAL INFORMATION:

(iii) NUMBER OF SEQUENCES: 23

(2) INFORMATION FOR SEQ ID NO: 1:

(i) SEQUENCE CHARACTERISTICS:
      (A) LENGTH: 354 base pairs
      (B) TYPE: nucleic acid
      (C) STRANDEDNESS: double
      (D) TOPOLOGY: linear (vii) IMMEDIATE SOURCE:
      (B) CLONE: D12

(ix) FEATURE:
      (A) NAME/KEY: CDS
      (B) LOCATION: 1..354

(xi) SEQUENCE DESCRIPTION: SEQ ID NO: 1:

```
GAGGTGCAGC TGGTGGAGTC TGGGGGAGGC TTGGTACAGC CTGGGGGGTC CCTGAGACTC      60

TCCTGTGCAG CCTCTGGAGT CACCTTTAGC AGCCATGCCA TGACCTGGGT CCGCCAGGCT     120

CCAGGGAAGG GGCTGGAATG GGTCTCAGGT ATCAGTGGTA GTGGTGGTGA CACATACCAC     180

GCAGACTCCG TGAAGGGCCG GTTCACCATC TCCAGGGACA ATTCCAAGAA CACGGTGTAT     240

CTGCAAATGA ACAGCCTGCG AGCCGAGGAC ACGGCCATAT ATTACTGTGC GATTTTAGGA     300

GTACTAAATG GTTTTGATAT CTGGGGCCAA GGGACAATGG TCACCTACTC CTCA           354
```

(2) INFORMATION FOR SEQ ID NO: 2:

(i) SEQUENCE CHARACTERISTICS:
      (A) LENGTH: 118 amino acids
      (B) TYPE: amino acid
      (D) TOPOLOGY: linear (vii) IMMEDIATE SOURCE:
      (B) CLONE: D12

(xi) SEQUENCE DESCRIPTION: SEQ ID NO: 2:

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Val Thr Phe Ser Ser His
            20                  25                  30

Ala Met Thr Trp Val Arg Gln Ala Pro Gly Lys Gly Leu Glu Trp Val
        35                  40                  45

Ser Gly Ile Ser Gly Ser Gly Gly Asp Thr Tyr His Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Ile Tyr Tyr Cys
            85                  90                  95

Ala Ile Leu Gly Val Leu Asn Gly Phe Asp Ile Trp Gly Gln Gly Thr
            100                 105                 110

Met Val Thr Tyr Ser Ser
            115
```

(2) INFORMATION FOR SEQ ID NO: 3:

(i) SEQUENCE CHARACTERISTICS:
        (A) LENGTH: 354 base pairs
        (B) TYPE: nucleic acid
        (C) STRANDEDNESS: double
        (D) TOPOLOGY: linear (vii) IMMEDIATE SOURCE:
        (B) CLONE: 1C (ix) FEATURE:
        (A) NAME/KEY: CDS
        (B) LOCATION: 1..354

(xi) SEQUENCE DESCRIPTION: SEQ ID NO: 3:

```
GAGGTGCAAC TGGTGGAAAG CGGGGGGGGC TTGGTACAGC CTGGGGGGTC CCTGAGACTC      60

TCCTGTGCAG CCTCTGGAGT CACCTTTANC AGCCATGCCA TGACCTGGGT CCNCCAGGCT     120

CCAGGGAAGG GGCTGGAATG GGTCTCAGGT ATCAGTGGTA GTGGTGGTGA CACANACCAC     180

GCGGACTCCG TGAAGGGCCG GTTCACCATC TCCAGGGACA ATTCCAAGAA CACGGTGTAT     240

CTCCAAATGA ACAGCCTGCG AGCCGAGGAC ACGGCCANAT ATTACTGTGC GATTTTAGGA     300

GTACTAAATG GTTTTGATAT CTGGGGCCAA GGGACAATGG TCACCTACTC CTCA           354
```

(2) INFORMATION FOR SEQ ID NO: 4:

(i) SEQUENCE CHARACTERISTICS:
        (A) LENGTH: 118 amino acids
        (B) TYPE: amino acid
        (D) TOPOLOGY: linear (vii) IMMEDIATE SOURCE:
        (B) CLONE: 1C (xi) SEQUENCE DESCRIPTION: SEQ ID NO: 4:

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Val Thr Phe Ser Ser His
            20                  25                  30

Ala Met Thr Trp Val Arg Gln Ala Pro Gly Lys Gly Leu Glu Trp Val
        35                  40                  45

Ser Gly Ile Ser Gly Ser Gly Gly Asp Thr Tyr His Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Ile Tyr Tyr Cys
                85                  90                  95

Ala Ile Leu Gly Val Leu Asn Gly Phe Asp Ile Trp Gly Gln Gly Thr
            100                 105                 110

Met Val Thr Tyr Ser Ser
        115
```

(2) INFORMATION FOR SEQ ID NO: 5:

(i) SEQUENCE CHARACTERISTICS:
        (A) LENGTH: 366 base pairs
        (B) TYPE: nucleic acid
        (C) STRANDEDNESS: double
        (D) TOPOLOGY: linear (vii) IMMEDIATE SOURCE:
        (B) CLONE: 2G (ix) FEATURE:

(A) NAME/KEY: CDS
        (B) LOCATION: 1..366

(xi) SEQUENCE DESCRIPTION: SEQ ID NO: 5:

GAGGTCAACT TAAGGGAATC TGGGGGAGGC TTGGTCAAGC CTGGAGGGTC CCTGAGACTC        60

TCCTGTGCAG CCTCTGGATT CACCTTCAGT GACTACTACA TGAGCTGGAT CCGCCAGGCT       120

CCAGGGAAGG GGCTGGAGTG GGTCTCAGCT ATTAGTGGTA GTGGTGGTAA CACATACTAC       180

GCAGACTCCG TGAAGGGCCG GTTCACCATC TCCAGAGACA ATTCCAAGAA CACNCTGTCT       240

CTCCAAATGA ACAGCCTGAG AACCGAGGAC ACGGCCCTAT ATTATTGTGT CAAAGGGGCC       300

CGAGCGGCTA GGGCCGGCGG GTACTTCGAT CTCTGGGGCC GTGGCACACT GGTCACCGTC       360

TCCTCA                                                                 366

(2) INFORMATION FOR SEQ ID NO: 6:

(i) SEQUENCE CHARACTERISTICS:
        (A) LENGTH: 122 amino acids
        (B) TYPE: amino acid
        (D) TOPOLOGY: linear (vii) IMMEDIATE SOURCE:
        (B) CLONE: 2G (xi) SEQUENCE DESCRIPTION: SEQ ID NO: 6:

Glu Val Asn Leu Arg Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Ala Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Ser
65                  70                  75                  80

Leu Gln Met Asn Ser Leu Arg Thr Glu Asp Thr Ala Leu Tyr Tyr Cys
                85                  90                  95

Val Lys Gly Ala Arg Ala Ala Arg Ala Gly Gly Tyr Phe Asp Leu Trp
            100                 105                 110

Gly Arg Gly Thr Leu Val Thr Val Ser Ser
        115                 120

(2) INFORMATION FOR SEQ ID NO: 7:

(i) SEQUENCE CHARACTERISTICS:
        (A) LENGTH: 360 base pairs
        (B) TYPE: nucleic acid
        (C) STRANDEDNESS: double
        (D) TOPOLOGY: linear (vii) IMMEDIATE SOURCE:
        (B) CLONE: 2Da (ix) FEATURE:
        (A) NAME/KEY: CDS
        (B) LOCATION: 1..360

(xi) SEQUENCE DESCRIPTION: SEQ ID NO: 7:

AGGGTGCAGC TGGTGGAGTC TGGGGGAGGC TTGGTACAGC CTGGCAGGTC CCTGAGACTC        60

TCCTGTGCAG CCTCTGGATT CACCTTTGAT GATTATGCCA TGCACTGGGT CCGGCAAGCT       120

CCAGGGAAGG GCCTGGAGTG GGTCTCAGGT ATTAGTTGGA ATAGTGGTAG CATAGGCTAT       180

```
GCGGACTCTG TGAAGGGCCG ATTCACCATC TCCAGAGACA ACGCCAAGAA CTCCCTGTAT      240

CTGCAAATGA ACAGTCTGAG AGCTGAGGAC ACGGCCGTGT ATTACTGTGC AAGACCGCTT      300

TATCCGAAGG GGACTCAGTA TGATTTTTGG GGCCAAGGTA CCCTGGTCAC CGTGTCCTCA      360

(2) INFORMATION FOR SEQ ID NO: 8:

(i) SEQUENCE CHARACTERISTICS:
        (A) LENGTH: 120 amino acids
        (B) TYPE: amino acid
        (D) TOPOLOGY: linear (vii) IMMEDIATE SOURCE:
        (B) CLONE: 2D (xi) SEQUENCE DESCRIPTION: SEQ ID NO: 8:

Arg Val Gln Leu Val Glu Ser Gly Gly Gly Leu Val Gln Pro Gly Arg
1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Leu Tyr Pro Lys Gly Thr Gln Tyr Asp Phe Trp Gly Gln
            100                 105                 110

Gly Thr Leu Val Thr Val Ser Ser
        115                 120

(2) INFORMATION FOR SEQ ID NO: 9:

(i) SEQUENCE CHARACTERISTICS:
        (A) LENGTH: 360 base pairs
        (B) TYPE: nucleic acid
        (C) STRANDEDNESS: double
        (D) TOPOLOGY: linear (vii) IMMEDIATE SOURCE:
        (B) CLONE: 2Db (ix) FEATURE:
        (A) NAME/KEY: CDS
        (B) LOCATION: 1..360

(xi) SEQUENCE DESCRIPTION: SEQ ID NO: 9:

GAGGTGCAGC TGGTGGAGTC TGGGGGAGGC TTGGTACAGC CTGGCAGGTC CCTGAGACTC       60

TCCTGTGCAG CCTCTGGATT CACCTTTGAT GATTATGCCA TGCACTGGGT CCGGCAAGCT      120

CCAGGGAAGG GCCTGGAGTG GGTCTCAGGT ATTAGTTGGA ATAGTGGTAG CATAGGCTAT      180

GCGGACTCTG TGAAGGGCCG ATTCACCATC TCCAGAGACA ACGCCAAGAA CTCCCTGTAT      240

CTGCAAATGA ACAGTCTGAG AGCTGAGGAC ACGGCCGTGT ATTACTGTGC AAGACCGCTT      300

TATCCGAAGG GGACTCAGTA TGATTTTTGG GGCCAAGGTA CCCTGGTCAC CGTGTCCTCA      360

(2) INFORMATION FOR SEQ ID NO: 10:

(i) SEQUENCE CHARACTERISTICS:
        (A) LENGTH: 120 amino acids
        (B) TYPE: amino acid
        (D) TOPOLOGY: linear
```

(vii) IMMEDIATE SOURCE:
    (B) CLONE: 2Db (xi) SEQUENCE DESCRIPTION: SEQ ID NO: 10:

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Leu Tyr Pro Lys Gly Thr Gln Tyr Asp Phe Trp Gly Gln
            100                 105                 110

Gly Thr Leu Val Thr Val Ser Ser
        115                 120

(2) INFORMATION FOR SEQ ID NO: 11:

(i) SEQUENCE CHARACTERISTICS:
        (A) LENGTH: 333 base pairs
        (B) TYPE: nucleic acid
        (C) STRANDEDNESS: double
        (D) TOPOLOGY: linear (vii) IMMEDIATE SOURCE:
        (B) CLONE: D12 (light chain)

(ix) FEATURE:
        (A) NAME/KEY: CDS
        (B) LOCATION: 1..333

(xi) SEQUENCE DESCRIPTION: SEQ ID NO: 11:

CAGTCTGCTC TGACTCAGCC TGCCTCTGTG TCTGGGTCTC CTGGACAGTC GATCACCATC      60

TCCTGCACTG GAACCAGCAG TGACGTTGGT GGTTATAAGT ATGTCTCCTG GTACCAACAG     120

CACCCAGGCA AAGCCCCCAA ACTCATGATT TTTGAGGTCA GTAATCGGCC CTCAGGGGTT     180

CCTAATCGCT TCTCAGGCTC CAAGTCTGGC AACACGGCCT CCCTGACCAT CTCTGGGCTC     240

CAGGTTGAGG ACGAGGCTGA TTATTACTGC AGCTCACTTA CACGCAGAGT CACTGTGATC     300

TTCGGCGGAG GGACCAAGCT GACCGTCCTA GGT                                   333

(2) INFORMATION FOR SEQ ID NO: 12:

(i) SEQUENCE CHARACTERISTICS:
        (A) LENGTH: 111 amino acids
        (B) TYPE: amino acid
        (D) TOPOLOGY: linear (vii) IMMEDIATE SOURCE:
        (B) CLONE: D12

(xi) SEQUENCE DESCRIPTION: SEQ ID NO: 12:

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Lys Tyr Val Ser Trp Tyr Gln Gln His Pro Gly Lys Ala Pro Lys Leu

```
                35                 40                 45
Met Ile Phe Glu Val Ser Asn Arg Pro Ser Gly Val Pro Asn Arg Phe
    50                  55                  60

Ser Gly Ser Lys Ser Gly Asn Thr Ala Ser Leu Thr Ile Ser Gly Leu
65                  70                  75                  80

Gln Val Glu Asp Glu Ala Asp Tyr Tyr Cys Ser Ser Leu Thr Arg Arg
                85                  90                  95

Val Thr Val Ile Phe Gly Gly Gly Thr Lys Leu Thr Val Leu Gly
                100                 105                 110

(2) INFORMATION FOR SEQ ID NO: 13:

(i) SEQUENCE CHARACTERISTICS:
        (A) LENGTH: 333 base pairs
        (B) TYPE: nucleic acid
        (C) STRANDEDNESS: double
        (D) TOPOLOGY: linear (vii) IMMEDIATE SOURCE:
        (B) CLONE: 1C/2D (ix) FEATURE:
        (A) NAME/KEY: CDS
        (B) LOCATION: 1..333

(xi) SEQUENCE DESCRIPTION: SEQ ID NO: 13:

CAGTCTGCTC TGACTCAGCC TGCCTCTGTG TCTGGGTCTC CTGGACAGTC GATCACCATC      60

TCCTGCACTG GAACCAGCAG TGACGTTGGT GGTTATAAGT ATGTCTCCTG GTACCAACAG     120

CACCCAGGCA AGCCCCCAA ACTCATGATT TTTGAGGTCA GTAATCGGCC CTCAGGGGTT     180

CCTAATCGCT TCTCAGGCTC CAAGTCTGGC AACACGGCCT CCCTGACCAT CTCTGGGCTC     240

CAGGCTGAGG ACGAGGCTGA TTATTACTGC AGCTCACTTA CACGCAGAGT CACTGTGATC     300

TTCGGCGGAG GGACCAAGCT GACCGTCCTA GGT                                   333

(2) INFORMATION FOR SEQ ID NO: 14:

(i) SEQUENCE CHARACTERISTICS:
        (A) LENGTH: 111 amino acids
        (B) TYPE: amino acid
        (D) TOPOLOGY: linear (vii) IMMEDIATE SOURCE:
        (B) CLONE: 1C/2D (xi) SEQUENCE DESCRIPTION: SEQ ID NO: 14:

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Lys Tyr Val Ser Trp Tyr Gln Gln His Pro Gly Lys Ala Pro Lys Leu
            35                  40                  45

Met Ile Phe Glu Val Ser Asn Arg Pro Ser Gly Val Pro Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Leu Thr Arg Arg
                85                  90                  95

Val Thr Val Ile Phe Gly Gly Gly Thr Lys Leu Thr Val Leu Gly
                100                 105                 110

(2) INFORMATION FOR SEQ ID NO: 15:
```

(i) SEQUENCE CHARACTERISTICS:
     (A) LENGTH: 326 base pairs
     (B) TYPE: nucleic acid
     (C) STRANDEDNESS: double
     (D) TOPOLOGY: linear (vii) IMMEDIATE SOURCE:
     (B) CLONE: 2G (ix) FEATURE:
     (A) NAME/KEY: CDS
     (B) LOCATION: 1..324

(xi) SEQUENCE DESCRIPTION: SEQ ID NO: 15:

```
GACATCGTGA TGACCCAGTC TCCATCTTCT GTGTCTGCAG CTATAGGCGA CACAATAACC    60

ATAACTTGTC GGGCGAGTCA CAATTTCAGG AGCTGGTTAG CCTGGTATCA GGTGAAACCT   120

GGAGAAGCCC CCAAGCCCCT GATCTACGGT GCATTCACTT TCCAAAATGG CGTCCCGTCC   180

AGATTCAGCG GCAGTGGCTC TGGGACAGAG TTCTCCCTCA CTATCAACAG CCTGCAGCTT   240

GACGATTTTG CAACTTACTT CTGTCAACAG GCTCACAGTT TCCCTCCCAC TTTCGGCGGA   300

GGGACCAAGC TGGAGATCAA ACGTGC                                       326
```

(2) INFORMATION FOR SEQ ID NO: 16:

(i) SEQUENCE CHARACTERISTICS:
     (A) LENGTH: 108 amino acids
     (B) TYPE: amino acid
     (D) TOPOLOGY: linear (vii) IMMEDIATE SOURCE:
     (B) CLONE: 2G (xi) SEQUENCE DESCRIPTION: SEQ ID NO: 16:

```
Asp Ile Val Met Thr Gln Ser Pro Ser Ser Val Ser Ala Ala Ile Gly
 1               5                  10                  15

Asp Thr Ile Thr Ile Thr Cys Arg Ala Ser His Asn Phe Arg Ser Trp
                20                  25                  30

Leu Ala Trp Tyr Gln Val Lys Pro Gly Glu Ala Pro Lys Pro Leu Ile
         35                  40                  45

Tyr Gly Ala Phe Thr Phe Gln Asn Gly Val Pro Ser Arg Phe Ser Gly
     50                  55                  60

Ser Gly Ser Gly Thr Glu Phe Ser Leu Thr Ile Asn Ser Leu Gln Leu
65                  70                  75                  80

Asp Asp Phe Ala Thr Tyr Phe Cys Gln Gln Ala His Ser Phe Pro Pro
                85                  90                  95

Thr Phe Gly Gly Gly Thr Lys Leu Glu Ile Lys Arg
                100                 105
```

(2) INFORMATION FOR SEQ ID NO: 17:

(i) SEQUENCE CHARACTERISTICS:
     (A) LENGTH: 217 base pairs
     (B) TYPE: nucleic acid
     (C) STRANDEDNESS: double
     (D) TOPOLOGY: linear (ix) FEATURE:
     (A) NAME/KEY: CDS
     (B) LOCATION: 35..205

(ix) FEATURE:
     (D) OTHER INFORMATION: /note= "pUC119Sfi polylinker region"

(xi) SEQUENCE DESCRIPTION: SEQ ID NO: 17:

```
AAGCTTTGGA GCCTTTTTTT TGGAGATTTT CAACGTGAAA AAATTATTAT TCGCAATTCC      60

TTTAGTTGTT CCTTTCTATG CGGCCCAGCC GGCCATGGCC CAGGTCCAAC TGCAGGTCGA     120

CCTCGAGATC AAACGGGCGG CCGCAGAACA AAAACTCATC TCAGAAGAGG ATCTGAATGG     180

GGCCGCACAT CACCATCATC ACCATTAATA AGGATCC                             217
```

(2) INFORMATION FOR SEQ ID NO: 18:

(i) SEQUENCE CHARACTERISTICS:
        (A) LENGTH: 57 amino acids
        (B) TYPE: amino acid
        (D) TOPOLOGY: linear (ix) FEATURE:
        (D) OTHER INFORMATION: /note= "pUC119Sfi polylinker
            region"

(xi) SEQUENCE DESCRIPTION: SEQ ID NO: 18:

```
Val Lys Lys Leu Leu Phe Ala Ile Pro Leu Val Val Pro Phe Tyr Ala
 1               5                  10                  15

Ala Gln Pro Ala Met Ala Gln Val Gln Leu Gln Val Asp Leu Glu Ile
            20                  25                  30

Lys Arg Ala Ala Ala Glu Gln Lys Leu Ile Ser Glu Glu Asp Leu Asn
        35                  40                  45

Gly Ala Ala His His His His His His
        50                  55
```

(2) INFORMATION FOR SEQ ID NO: 19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid; ssDNA (ix) FEATURE:
        (D) OTHER INFORMATION: /note= "Primer FDTSEQ"

(xi) SEQUENCE DESCRIPTION: SEQ ID NO: 19:

```
GTCGTCTTTC CAGACGTTAG T                                               21
```

(2) INFORMATION FOR SEQ ID NO: 20:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Other nucleic acid; ssDNA (ix) FEATURE:
        (D) OTHER INFORMATION: /note= "Primer pUC19REVERSE"

(xi) SEQUENCE DESCRIPTION: SEQ ID NO: 20:

```
AGCGGATAAC AATTTCACAC AGG                                             23
```

(2) INFORMATION FOR SEQ ID NO: 21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear -continued (ii) MOLECULE TYPE: Other nucleic acid; ssDNA (ix) FEATURE:
    (D) OTHER INFORMATION: /note= "MYCSEQ10"

(xi) SEQUENCE DESCRIPTION: SEQ ID NO: 21:

CTCTTCTGAG ATGAGTTTTT G          21

(2) INFORMATION FOR SEQ ID NO: 22:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: Other nucleic acid; ssDNA (ix) FEATURE:
       (D) OTHER INFORMATION: /note= "Primer PCR-L-LINK"

(xi) SEQUENCE DESCRIPTION: SEQ ID NO: 22:

GGCGGAGGTG GCTCTGGCGG T          21

(2) INFORMATION FOR SEQ ID NO: 23:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: Other nucleic acid; ssDNA (ix) FEATURE:
       (D) OTHER INFORMATION: /note= "Primer PCR-H-LINK"

(xi) SEQUENCE DESCRIPTION: SEQ ID NO: 23:

ACGGCCAGAG CCACCTCCGC C          21